United States Patent [19]

Trani et al.

[11] Patent Number: 5,561,057
[45] Date of Patent: Oct. 1, 1996

[54] **RESOLUTION OF (RS)-IBUPROFEN BY *CANDIDA ANTARCTICA* CATALYZED ESTERIFICATION WITH LONG CHAIN ALCOHOLS WHILE REMOVING WATER**

[75] Inventors: Michael Trani, Lasalle, Canada; Françoise Ergan, Amiens, France; Robert Lortie, Outremont, Canada

[73] Assignee: National Research Council of Canada, Ottawa, Canada

[21] Appl. No.: 309,434

[22] Filed: Sep. 20, 1994

[51] Int. Cl.⁶ .................................................. C07C 15/02
[52] U.S. Cl. ............................................................ 435/280
[58] Field of Search ............................................. 435/280

[56] References Cited

U.S. PATENT DOCUMENTS 5,169,780  12/1992  Stirling et al. ........................ 435/280
5,273,898  12/1993  Ishii ...................................... 435/198

OTHER PUBLICATIONS

Eigtved P et al, Proc. World Conf. Biotechnol. Fats Oils Ind. (1988) Eds. Applewhite T. H. pp. 134–137.
Arroyo M et al, J. Org. Chem. 59:4410–17 (1994).

*Primary Examiner*—Michael G. Wityshyn
*Assistant Examiner*—S. Saucier
*Attorney, Agent, or Firm*—J. Wayne Anderson

[57] ABSTRACT

The invention disclosed relates to a process for the enzymatic esterification and transesterification of racemic carboxylic acids and alcohols in which the reaction products predominantly include the ester of the more reactive acid or alcohol enantiomer and the less reactive acid or alcohol enantiomer, wherein the reactions are effected, preferably in a solventless medium, and the by-product water or short-chain alcohol is removed as it is formed.

6 Claims, 5 Drawing Sheets

○ total ester concentration
△ (R)-ibuprofen concentration
▽ (S)-ibuprofen concentration ● (R)-ibuprofen concentration
■ (S)-ibuprofen concentration ■ (R)-propranolol ● (S)-propranolol

RESOLUTION OF (RS)-IBUPROFEN BY *CANDIDA ANTARCTICA* CATALYZED ESTERIFICATION WITH LONG CHAIN ALCOHOLS WHILE REMOVING WATER

BACKGROUND OF THE INVENTION

1. Field of the Invention

This invention relates to the enzymatic esterification of racemic carboxylic acids and racemic alcohols, and to the transesterification of alcohols, wherein resolution of the racemic acids and alcohols is provided.

Optical isomers (or enantiomers) are molecules that are mirror images one of the other and cannot be superimposed. They exist because of the presence of asymmetry in their structure, typically involving an asymmetric carbon atom.

Their physico-chemical properties are identical except for in the direction of rotation of the plane of polarized light and their interaction with other asymmetric molecules. This renders the separation of optical isomers difficult.

Optical purity, the presence of only one optical isomer, of chemicals used as drugs is important because the molecules with which drugs interact—receptors, enzymes, etc.—are asymmetric and therefore may behave differently with the two isomers. In some cases, the non-active isomer is responsible for important side effects.

2. Description of the Prior Art

The separation of optical isomers can be achieved by the classical precipitation of diastereoisomers (Willen, S. H., Collet, A. and Jacques, J., *Tetrahedron*, 33, 2725–2736, (1977), or by kinetic resolution, using chemical reaction (Katsuki, T. and Sharpless. K. B., *J. Am. Chem. Soc.*, 102 5974–5976 (1980), chemical (Martin, V. S., Woodard, S. S., Katsuki, T., Yamada, Y., Ikeda, M. and Sharpless K. B., *J. Am. Chem. Soc.*, 103, 6237–6240 (1981) or enzymatic catalysis. Margolin, A. L., *Enzyme Microbial Technol.* 15, 266–280 (1993).

Enzymatic resolution is based on the difference in the rates of the reactions catalyzed by an enzyme on the two isomers of the molecule of interest. It can be performed either through hydrolysis, synthesis, oxidation or group transfer, depending on the functions present on the molecule.

In the case of racemic acids and alcohols, the esterase catalyzed stereoselective hydrolysis of esters has been extensively described (in the example shown in scheme I below, the acid moiety of the ester bears the asymmetric centre and the (R)-acid and (S)-ester can be separated by classical methods).

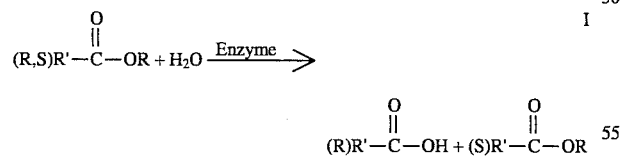

The esterification or transesterification in organic or aqueous/organic media has also been described. In scheme II below, the (S)-acid is esterified to produce the (S)-ester and leave (R)-acid untouched. In reaction scheme IIA below, if the alcohol bears the asymmetric centre and the (S)-form of the alcohol reacts in the esterification, the (R)-form remains untouched and the (S)-ester is produced.

In scheme III, the alcohol bears the asymmetric centre and the (S)-form of the alcohol reacts in the transesterification while the (R)-form remains untouched.

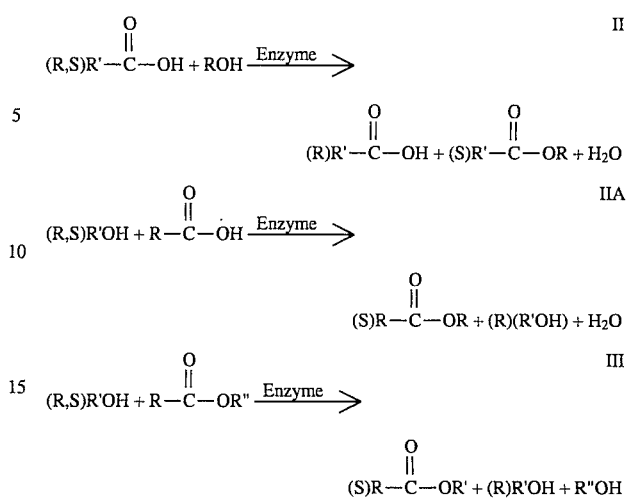

In the above reaction schemes II, IIA and III R is an alkyl group containing 8 or more carbon atoms for acids, and containing 10 or more carbon atoms for alcohols and esters, (i.e. long enough so that the vapour pressure of the alcohol, acid or ester is low at the temperature of the reaction and the alcohol does not evaporate). R is an alkyl group which may be saturated or unsaturated, linear or branched, substituted or unsubstituted, an aryl group which may be substituted or unsubstituted, heterocyclic, substituted or unsubstituted, or any other group that does not contain a chemical function that will react with the alcohol ROH or acid RCOOH, and R" is a lower alkyl group containing 1 to 4 carbon atoms (to allow the easy evaporation of the by-product alcohol, R" OH formed during the transesterification reaction).

The following limitations or drawbacks of present apparatus, product or process, are noted.

For acids and alcohols, aqueous hydrolysis is limited to esters that are soluble in water. Aqueous/organic two phase systems can be used to overcome this limitation at the expense of increased complexity.

Esterification and transesterification in organic solvents or two phase aqueous/organic systems have to overcome yield limitation caused by the by-product of the reaction, namely, water or short-chain alcohol ($R^{11}OH$).

SUMMARY OF THE INVENTION

According to the invention, a process for the enzymatic esterification of racemic carboxylic acids and racemic alcohols, and the enzymatic transesterification of racemic alcohols is provided, comprising (a) subjecting a racemic carboxylic acid to esterification with a long-chain fatty alcohol having ten or more carbon atoms, preferably in a solventless medium, in the presence of an enzyme which catalyzes the formation of ester bonds while removing the by-product water as it is formed, whereby a reaction product is formed which is enriched in an ester of the more reactive acid enantiomer and in the less reactive acid enantiomer, or (b) subjecting a racemic carboxylic alcohol to esterification with a carboxylic acid having eight or more carbon atoms, preferably in a solventless medium, in the presence of an enzyme which catalyzes the formation of ester bonds while removing the by-product water as it is formed, whereby a reaction product is formed which is enriched in an ester of the more reactive alcohol enantiomer and in the less reactive alcohol enantiomer, or (c) subjecting a racemic carboxylic alcohol to transesterification with a long-chain carboxylic acid ester having ten or more carbon atoms, preferably in a solventless medium, in the presence of an enzyme which catalyzes the formation of ester bonds while removing the by-product short-chain alcohol as it is formed, whereby a reaction product is formed which is enriched in an ester of the more reactive alcohol enantiomer and in the less reactive alcohol enantiomer.

To separate optical isomers through enzymatic esterification or transesterification, preferably in solventless media, using molten substrates and applying vacuum to remove the water or short chain alcohol produced by the reaction. The use of long chain (8 carbon atoms or more in the case of acids and 10 carbon atoms or more in the case of alcohols and esters) alcohols or acids permits to lower the pressure (to about ≦mbar for esterification and to about 6–7 mbar for transesterification) without excessive evaporation.

By contacting an esterase or an enzyme having esterase activity with the racemic acid and a long chain alcohol or with the racemic alcohol and a long chain acid, it is possible to obtain ester synthesis in good yield if the water produced by the reaction is removed as it is formed. This is also true for the transesterification between a racemic alcohol and a long chain ester of which the alcohol moiety has a high vapor pressure at the temperature of the reaction.

Depending on the stereoselectivity of the enzyme, the product or the substrate can be enriched in one of the two isomers of the chiral substrate.

Two examples are given below.

Example 1

Resolution of (R,S)-ibuprofen.

(R,S)-ibuprofen was esterified with fatty alcohols (C10–C18). The reaction was catalyzed by *Candida antarctica* type A and B lipases immobilized on acrylic resin support and produced under the name of SP382 by Novo Industries (Denmark) or by *Candida antarctica* type B lipase immobilized on acrylic resin and produced under the name NOVOZYM 435, also by Novo Industries. The catalytic activity of the lipase is higher with the (R) form of ibuprofen and, therefore, it is possible to enrich the reaction mixture in (S)-ibuprofen, as shown in FIG. 1.

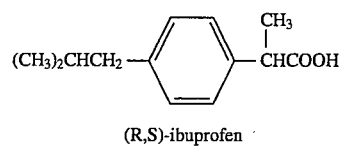

(R,S)-ibuprofen

Figure 1A:
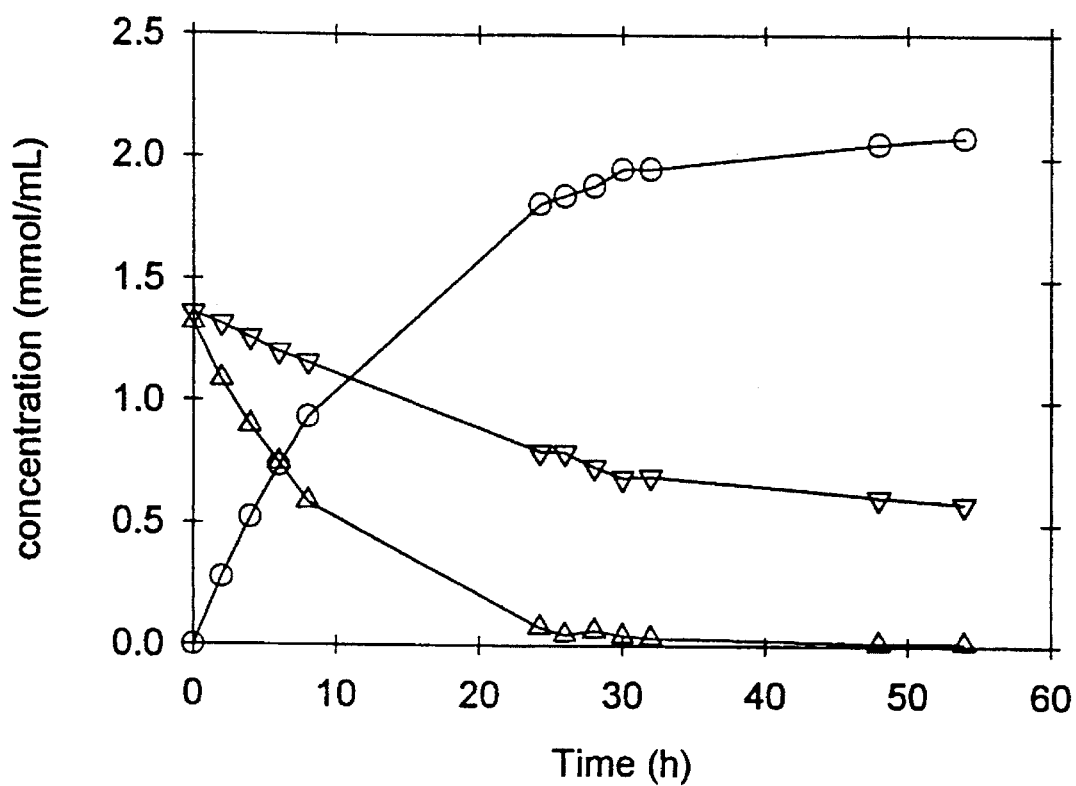
FIGS. 1A and 1B are graphical representations of the time course of an esterification reaction illustrative of the invention.

Specifically, FIG. 1A represents the time course of the following esterification reaction.

2 g (R,S)-ibuprofen+ 0.333 g SP382 1.76 g hexadecanol. T=60° C., p≦1 mbar

Figure 1B:
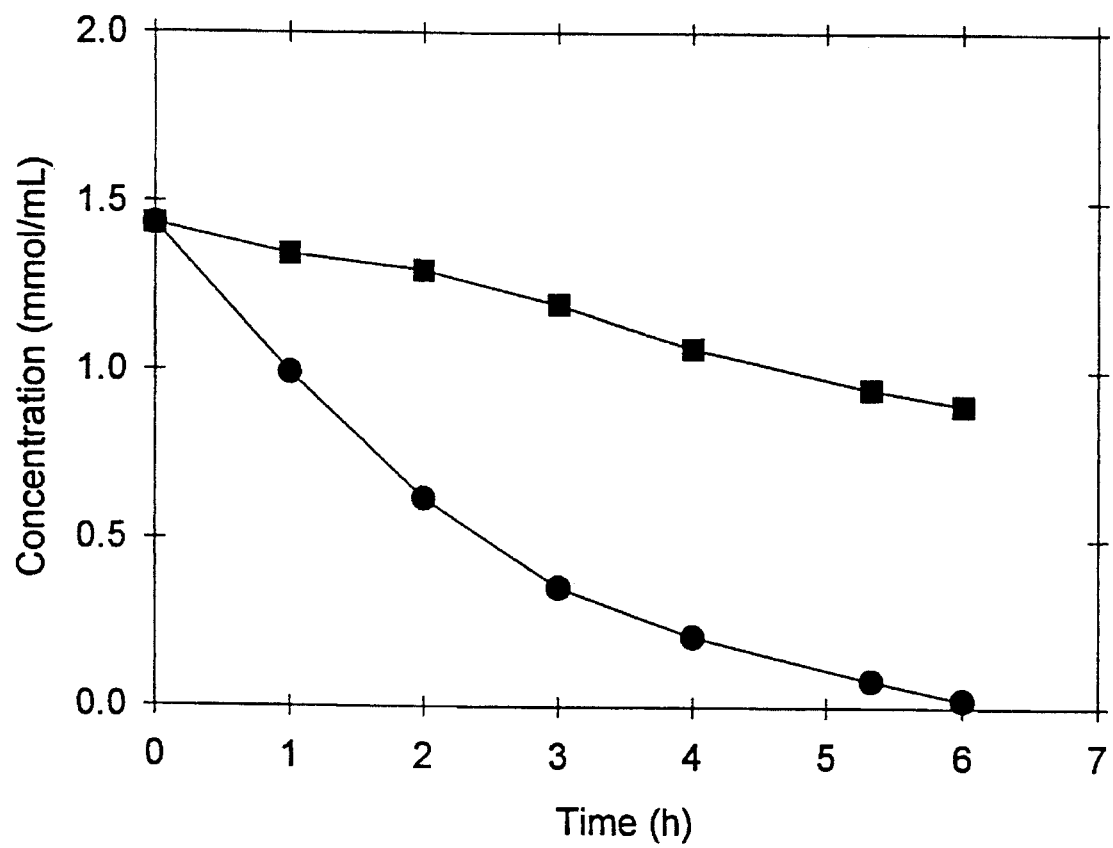

FIG. 1B represents the time course of the following esterification reaction.

10 g (R,S)-ibuprofen+3.333 g NOVOZYM 435+5.755 g decanol. T=70° C., p≦1 mbar.

Figure 2:
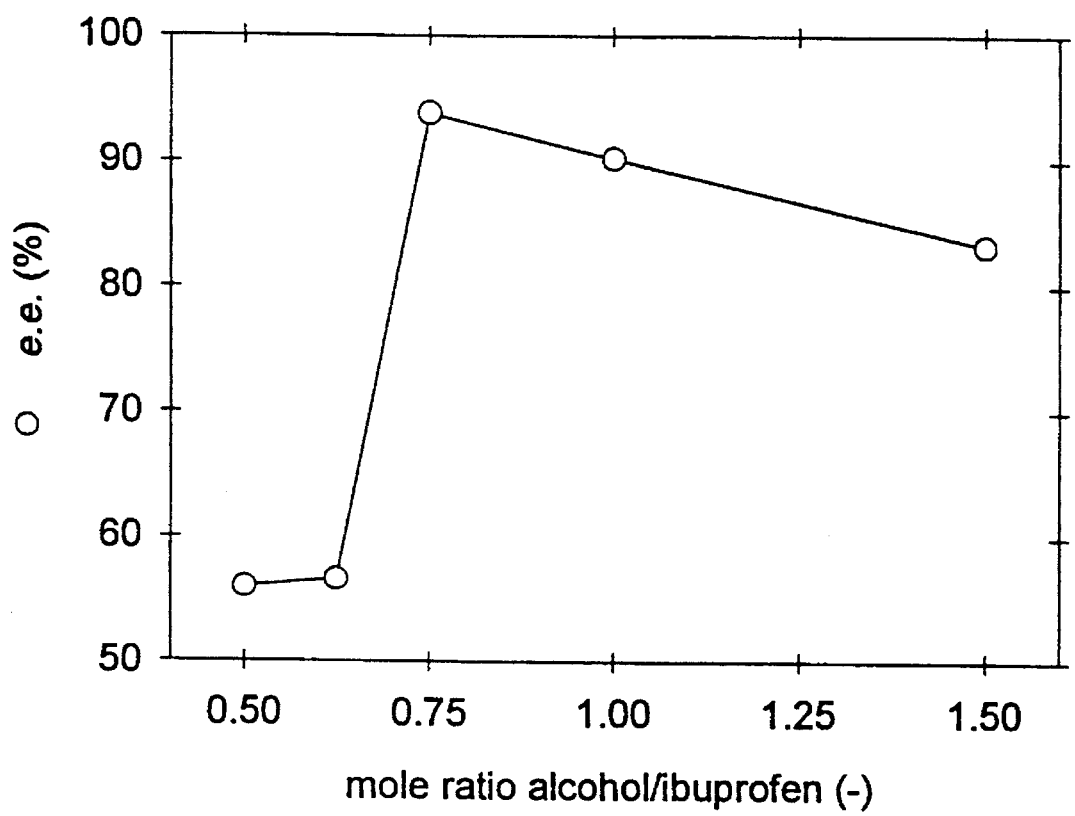
FIG. 2 is a graph representing the effect of the ratio of alcohol to acid in an esterification reaction illustrative of the invention.

Different alcohol to ibuprofen ratios were tested, and FIG. 2 shows the effect of this ratio on the enantiomeric excess of (S)-ibuprofen (e.e.)

Also, the effect of the ratio alcohol/ibuprofen on the maximum enantiomeric excess measured in the following reaction is shown:

2 g (R, S) -ibuprofen+0.333 g SP382 T=60° C. , p≦1 mbar

Alcohol=hexadecanol.

Accordingly, a useful mole ratio range of 0.5 to 1.5 is contemplated, with about 0.75 being preferred.

Figure 3:
FIG. 3 is a graph representing the effect of alcohol chain length in an esterification reaction illustrative of the invention.

Different alcohol chain lengths were also used. FIG. 3 shows the effect of the chain length on the maximum enantiomeric excess measured.

Specifically, the effect of alcohol chain length on the maximum e.e. measured is illustrated in the following reaction.

2 g (9.69 mmol) (R,S)-ibuprofen+0.333 g SP382+7.27 mmol alcohol.

T=60° C., p≦1 mbar.

Accordingly, there is not much difference in effect from 10 to 18 carbon atoms, with about 12 carbon atoms being preferred.

Example 2

Resolution of (R,S)-propranolol.

Figure 4:
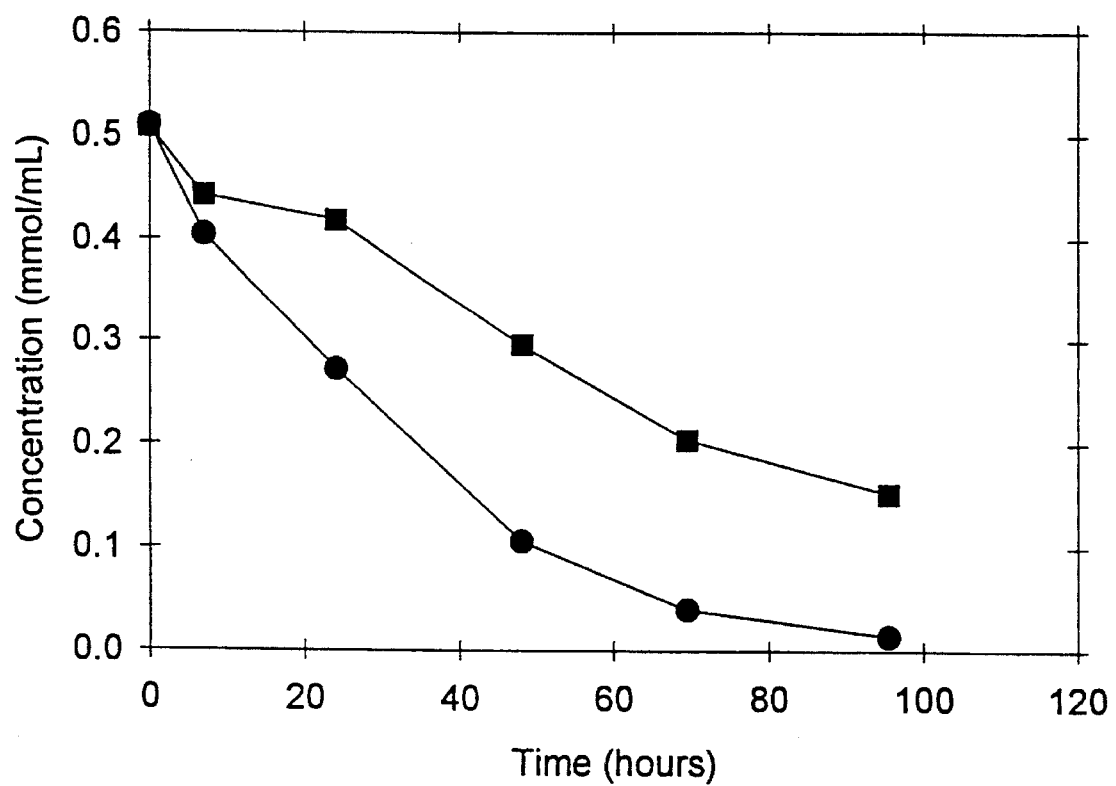
FIG. 4 is a graph representing the time course of a transesterification reaction illustrative of the invention.

Propranolol was transesterified with methyl esters of fatty acids (C16–C22). The reaction was catalyzed by *Candida antarctica* type B lipase immobilized on acrylic resin and produced under the name of NOVOZYM 435 by Novo Industries (Denmark). The catalytic activity of the lipase is higher with the (S)form of propranolol and therefore, it is possible to enrich the reaction mixture in (R)-propranolol, as shown in FIG. 4.

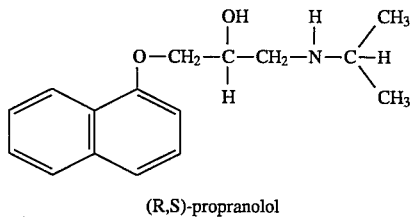

(R,S)-propranolol

Specifically, the transesterification of (R,S)-propranolol with palmitic acid methyl ester catalyzed by NOVOZYM 435, according to the following reaction, is illustrated.

0.75 g propranolol+2.086 g palmitic acid methyl ester+ 0.2 g enzyme.

T=75° C., p=6 to 7 mbar.

We claim:

1. A process for the resolution of (R,S)-ibuprofen by stereoselective enzymatic esterification, comprising subjecting (R,S)-ibuprofen to esterification with a long-chain fatty alcohol having ten or more carbon atoms, the molar ratio of alcohol to acid being 0.5 to 1.5, in a medium free of additional solvent in the presence of lipase A and B from *Candida antarctica* which catalyzes the formation of ester bonds while removing the by-product water as it is formed, whereby a reaction product is formed which is enriched in an ester of the more reactive acid enantiomer.

2. The process according to claim 1, wherein the by-product water is removed by reduced pressure.

3. The process according to claim 1, wherein the by-product water is removed by means of reduced pressure of $\leq 1$ mbar.

4. The process according to claim 3, wherein the long-chain alcohol has 10–18 carbon atoms.

5. The process according to claim 1, wherein the lipase is immobilized on an acrylic resin support.

6. The process according to claim 5, wherein the molar ratio of alcohol:acid is about 0.75, the long-chain alcohol is hexadecanol and the reaction temperature is 60° C.

* * * * *